(12) United States Patent
Rowe et al.

(10) Patent No.: US 8,235,922 B2
(45) Date of Patent: Aug. 7, 2012

(54) IDENTIFICATION MEANS

(75) Inventors: Christopher Rowe, Amersham (GB); Jan Huyser, Biggleswade (GB); Simon Michael Roff, Dunstable (GB)

(73) Assignee: Huntleigh Technology Limited (GB)

( * ) Notice: Subject to any disclaimer, the term of this patent is extended or adjusted under 35 U.S.C. 154(b) by 1119 days.

(21) Appl. No.: 12/093,724

(22) PCT Filed: Nov. 7, 2006

(86) PCT No.: PCT/GB2006/004154
§ 371 (c)(1),
(2), (4) Date: May 15, 2008

(87) PCT Pub. No.: WO2007/057639
PCT Pub. Date: May 24, 2007

(65) Prior Publication Data
US 2008/0281241 A1    Nov. 13, 2008

(30) Foreign Application Priority Data
Nov. 15, 2005 (GB) .................................. 0523249.1

(51) Int. Cl.
*A61H 7/00* (2006.01)
(52) U.S. Cl. ........................................ 601/151; 601/152
(58) Field of Classification Search ................ 601/152; 602/13; 128/DIG. 20; 600/490, 495
See application file for complete search history.

(56) References Cited

U.S. PATENT DOCUMENTS

| 4,501,280 A * | 2/1985 | Hood, Jr. ..................... 600/490 |
| 5,003,981 A * | 4/1991 | Kankkunen et al. .......... 600/490 |
| 5,060,654 A | 10/1991 | Malkamaki et al. |
| 5,144,956 A * | 9/1992 | Souma ......................... 600/495 |
| 5,301,676 A | 4/1994 | Rantala et al. |
| 2003/0093001 A1 | 5/2003 | Martikainen |

FOREIGN PATENT DOCUMENTS

| EP | 1 310 210 A | 5/2003 |
| EP | 1310210 A2 | 5/2003 |

* cited by examiner

*Primary Examiner* — Michael A. Brown
(74) *Attorney, Agent, or Firm* — Craig A. Fieschko, Esq.; DeWitt Ross & Stevens S.C.

(57) ABSTRACT

A pump supplies pressurized air to inflate compression garments, mattresses, cushions, or similar at the desired times and to desired pressures appropriate to the therapy. The garments are each identified by small steps generated in the pressure waveform during inflation, with the identifying means including a flat sheet valve in the connector chamber having vents to atmosphere and being situated along the flow path from the pump to the garment(s). As the air flows through the connection tubing and through the connector a pressure wave is generated by the valve and fed back upstream to a pressure sensor in the pump. The shape of the pressure waveform identifies a particular compression garment, the pump supplying the appropriate inflation regime upon detection of this pressure waveform.

12 Claims, 7 Drawing Sheets

IDENTIFICATION MEANS

FIELD OF THE INVENTION

The present invention relates to a device supplying pressurised air to an inflatable article and in particular to means in such a device for identifying the article connected.

BACKGROUND OF THE INVENTION

Existing methods for identifying the article connected to a pump include RFIDs as well metal inserts located in the article connectors. The known methods are expensive and require additional connector parts to operate.

SUMMARY OF THE INVENTION

The invention seeks to make improvements.

Accordingly, the invention provides a pump supplying pressurised air to an inflatable article and means for identifying the article connected by way of a pressure waveform generated as the article is initially inflated. According to a preferred embodiment of the invention, the identification means is connected to a compression garment supplied with pressurised air from a pump. According to another preferred embodiment of the invention the identification means is connected to an inflatable support surface, such as a mattress or cushion. Preferably, pressure recordings taken from a pressure sensor in the pump identify the garment or inflatable support surface connected to the pump. Preferably, the identification means is located in the connector, such that as the air flows down the connection tubing and through the connector a pressure wave is mechanically generated and fed back upstream to the pressure sensor. As there are no wires in the system the technique will work with ordinary extension tubing. The identification means generates easily detectable pressure waveform shapes that are detected upstream by the pressure sensor in the pump and advantageously does not effect the inflation applied to the garment or similar article.

BRIEF DESCRIPTION OF THE DRAWINGS

An example of the invention will now be described with reference to the accompanying drawings, in which.

DETAILED DESCRIPTION OF PREFERRED EMBODIMENTS OF THE INVENTION

Figure 1:
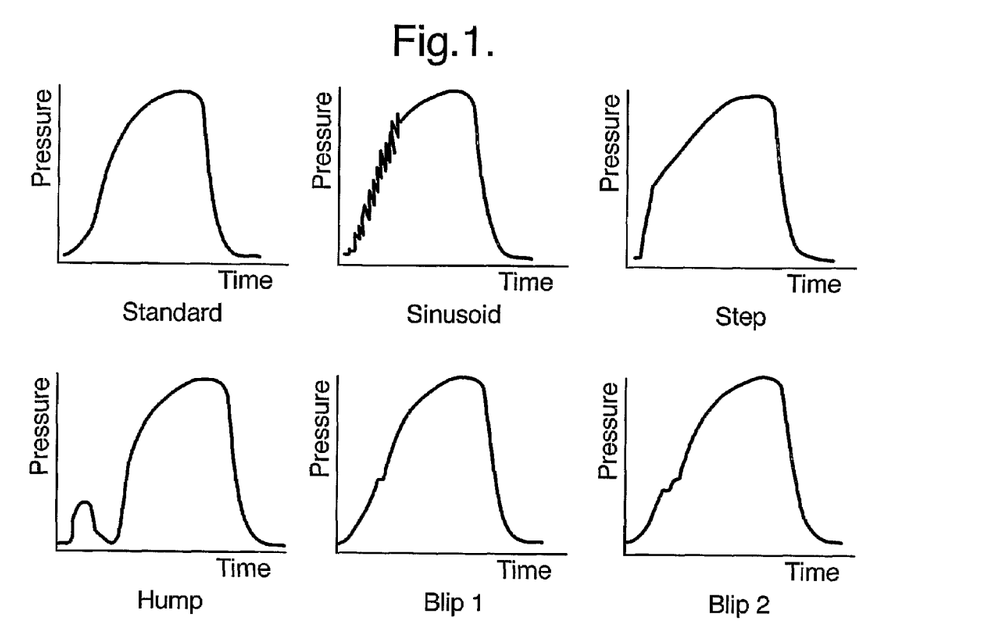
FIG. 1 shows a schematic representation of pressure waveforms generated by an identification means according to the invention.
Figure 2:
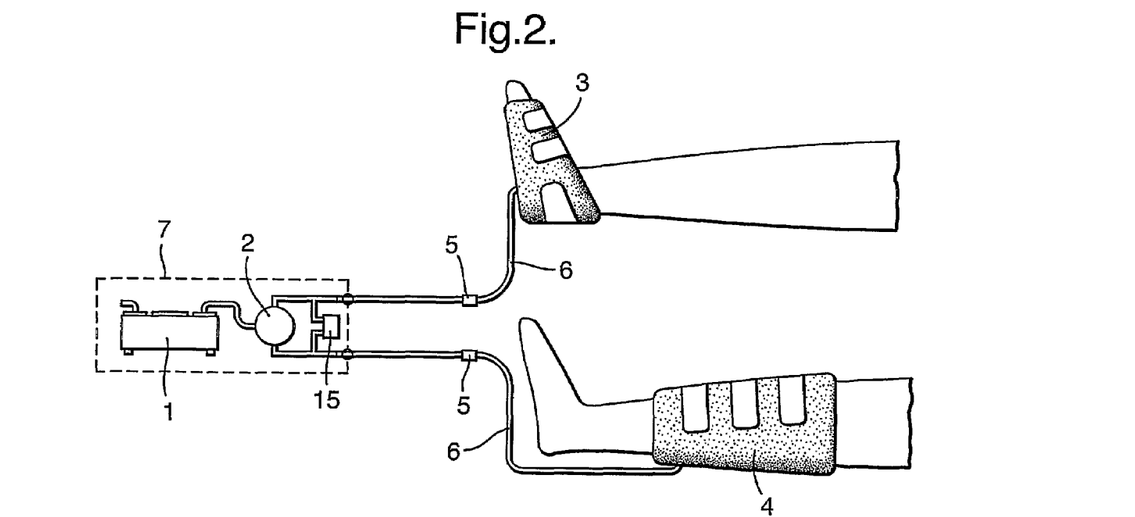
FIG. 2 is a schematic representation of a preferred embodiment of the invention.
Figure 5:
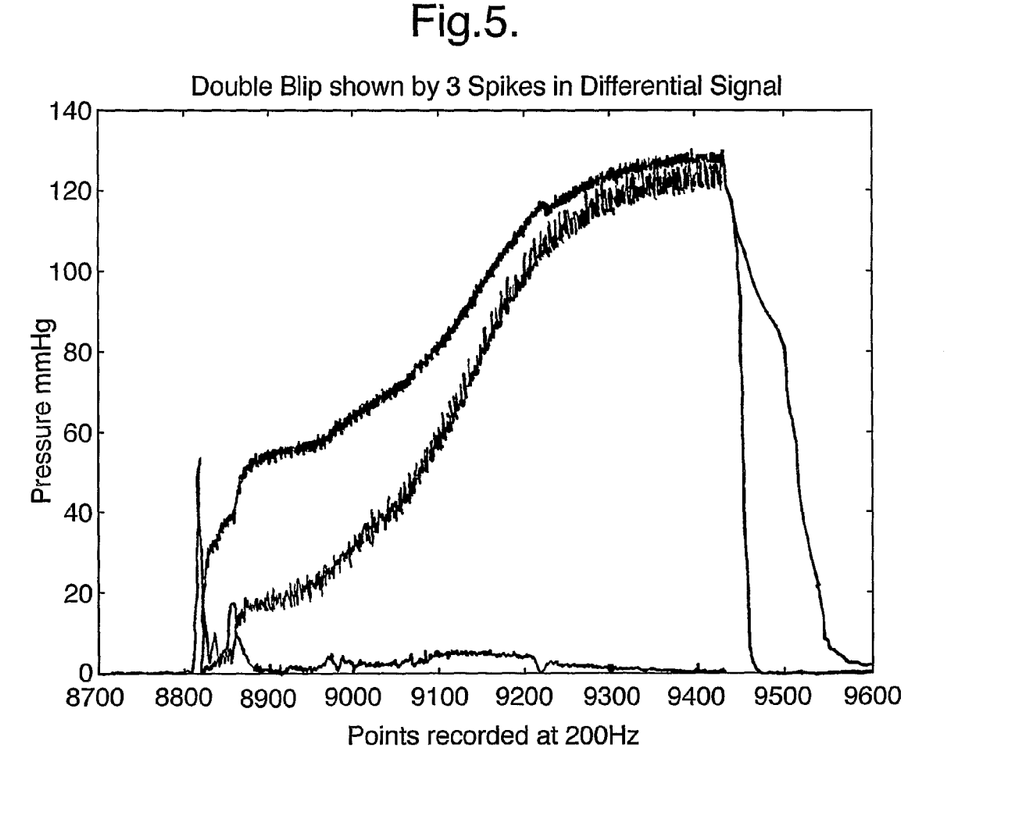
FIG. 5 shows another identifying pressure wave according to the invention, wherein the trace of greatest magnitude shows pump pressure, the trace of intermediate magnitude shows garment pressure, and the trace of lowest magnitude shows the derivative of the garment pressure.
Figure 6:
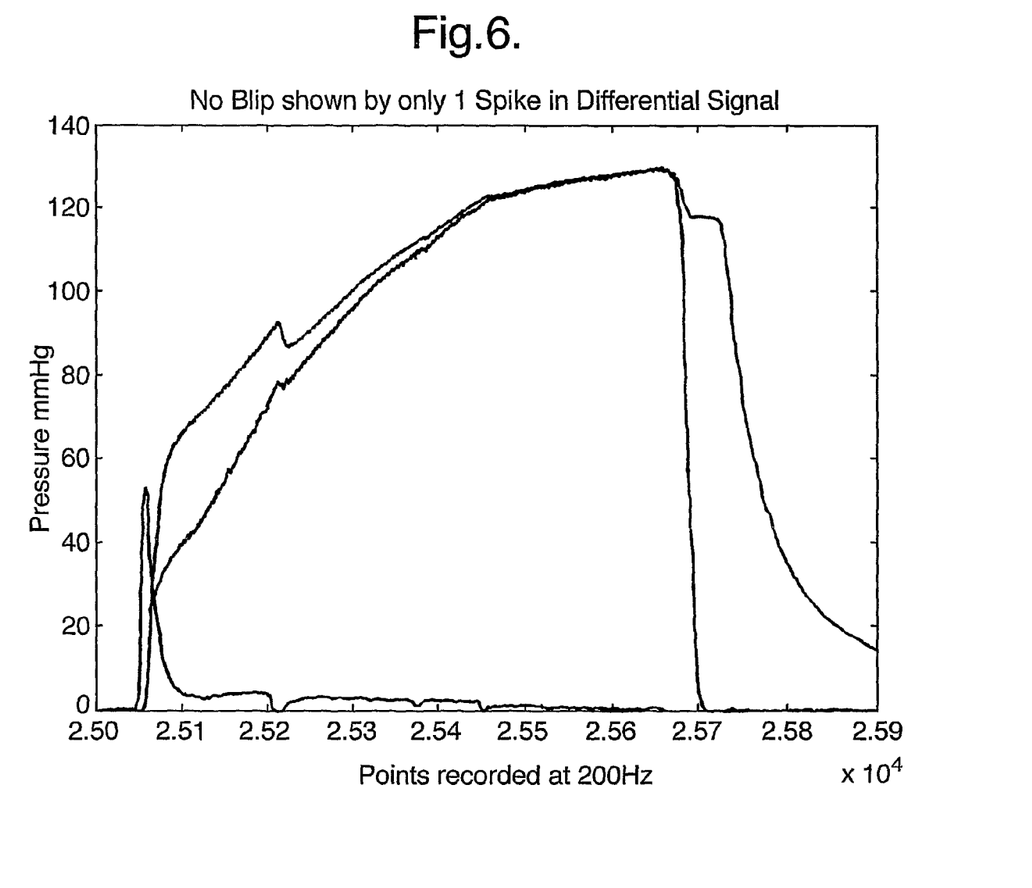
FIG. 6 shows a pressure wave of the prior art, wherein the trace of greatest magnitude shows pump pressure, the trace of intermediate magnitude shows garment pressure, and the trace of lowest magnitude shows the derivative of the garment pressure.

Referring to the Figures, there are several waveform shapes that are generated, some examples illustrated in FIG. 1. A preferred embodiment of the invention applies the identification means to a compression garment and pump system as shown in FIG. 2. A compressor 1 forces air via a pressure control unit, for example a rotor and stator unit 2 to inflate the garments 3, 4 at the desired times and to the desired pressures appropriate to the therapy. The foot garment 3 is inflated to 130 mmHg for a short period of one second whilst the calf garments 4 (or thigh garment, not shown) are inflated to only 40 mmHg but the pressure is held for a longer period say, eight seconds. The garments 3, 4 are each identified by very small steps generated in the waveform during inflation, the identification means in this example showing one step for the calf garment (see FIG. 4) and two steps for the foot garment 3 (see FIG. 5). FIG. 6 shows the inflation of a foot garment without the identification means where only the initial spike of initiating inflation is seen without any of the differentiating steps thereafter.

The identification means 9 creating the waveform steps can be located anywhere along the tubing 6 and it may be advantageous to locate it at the end of the tubing 6 where it joins to the garment or similar inflatable article as it will prevent non authorised use of the system.

Figure 7:
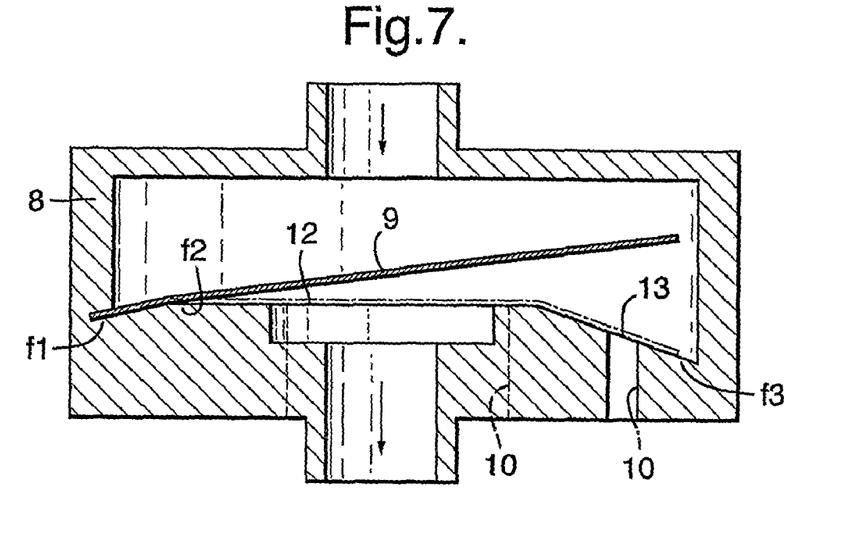
FIG. 7 shows the identification means according to the invention.
Figure 8:
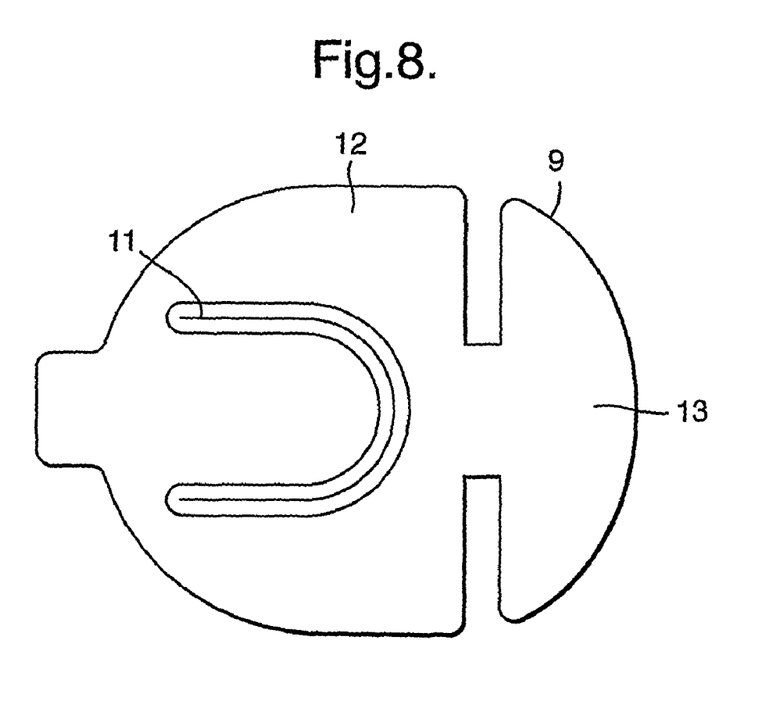
FIG. 8 shows a valve of the identification means.
Figure 9:
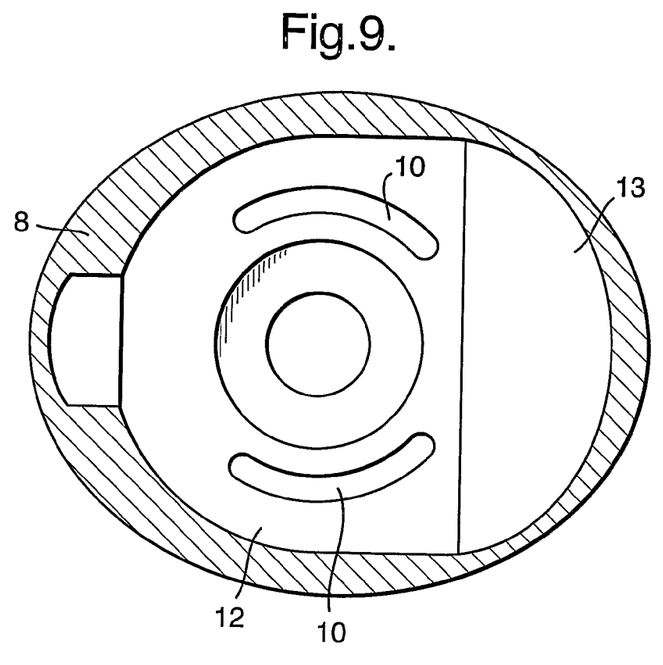
FIG. 9 shows one connector according to the invention.

As shown in FIG. 7, the identification means 9 is located within the connector 5 in the preferred embodiment. The identification means consists of a main flat sheet valve 9 in the connector chamber 8 having several vents 10 to atmosphere and comprising the main flow path from the compressor 1 to the garment (s) 3, 4. The main flat sheet valve 9 has two sections 12 and 13 that are free to bend independently with a firmness dependent on the sheet material and the geometry of the valve. It also has a 'horseshoe' flap 11 that opens up under pressure allowing air flow into the garments 3, 4, as shown in FIGS. 8-9.

In use, upon initiation of inflation, the air travels into the chamber 8 and then following the path of least resistance the air flows out of the vents 10 to atmosphere rather than into the garment(s) 3, 4. At the same time, the sheet valve 9 that is open at a set mounting angle within the chamber 8 is forced shut by the air flowing around it. The horseshoe flap 11 is shut at this time so the air pushes the main valve 9 as if it were a single solid sheet. In the one step connector (as shown in FIG. 9) as the main valve 9 shuts, section 12 cuts off all the vents 10 to atmosphere, the pressure in the chamber 8 builds up and the horseshoe flap 11 opens allowing the garment 3, 4 to inflate as normal.

Figure 4:
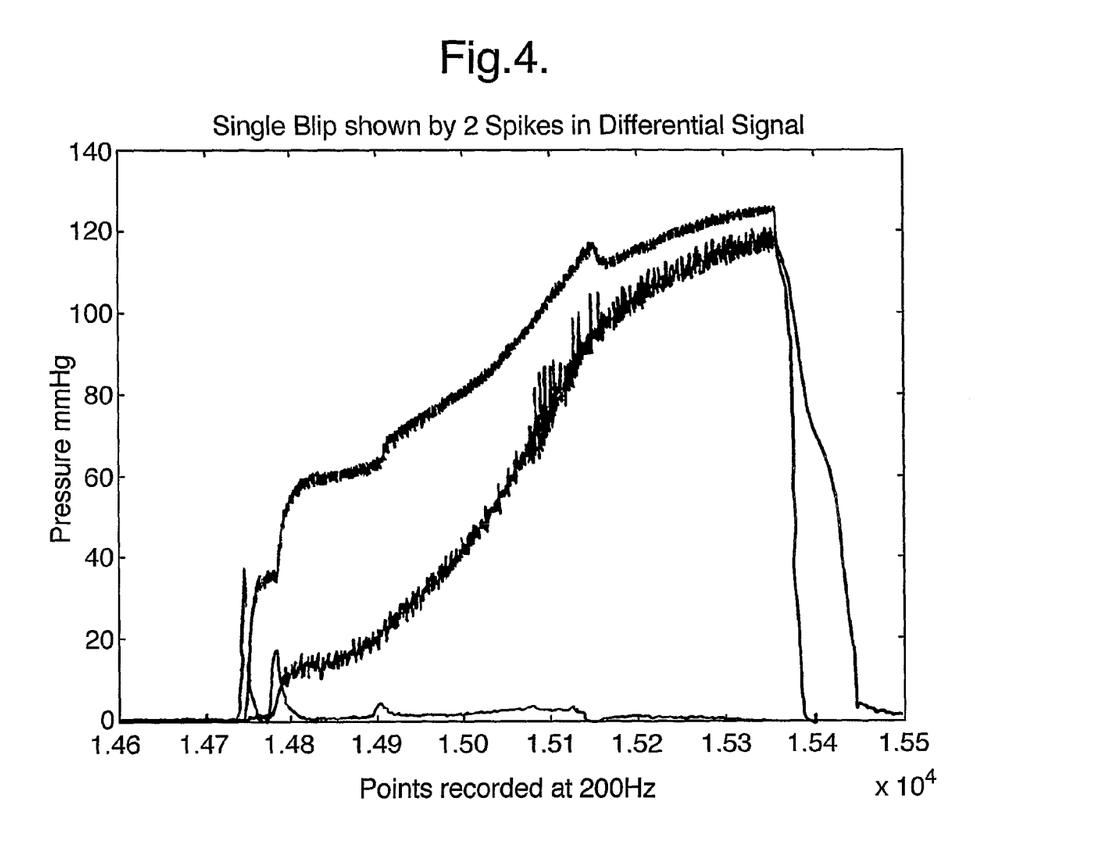
FIG. 4 shows an identifying pressure wave according to the invention, wherein the trace of greatest magnitude shows pump pressure, the trace of intermediate magnitude shows garment pressure, and the trace of lowest magnitude shows the derivative of the garment pressure.

This results in a single step being produced in the waveform detected by the pressure sensor 15 in the pump unit 7, as shown in FIG. 4. A very simple method to detect this step is to differentiate the signal and count the spikes, in this case two spikes for the one step.

Figure 10:
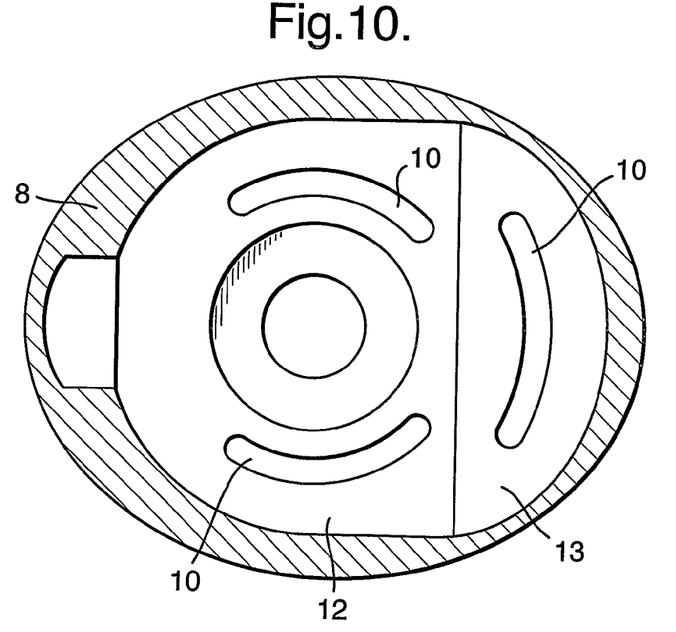
FIG. 10 shows another connector according to the invention.

In the two step version (FIGS. 8 and 10) not all the vents 10 to atmosphere are cut off by section 12, it is only after the next stage when section 13 is forced down that all the vents 10 to atmosphere are cut off and the horseshoe flap 11 opens. This results in two steps in the waveforms and three spikes counted in the differential signal, as seen in FIG. 5.

The pump 7 initially inflates to detect either one or two steps, and depending on the number of steps detected, the pump provides the appropriate pre-set therapy. If the garments 3 or 4 are changed whilst the pump 7 is turned on it will detect the change in steps before complete inflation and change the therapies. If a standard connector is used then there are no steps detected apart from the initial spike as shown in FIG. 6 and no therapy will be supplied by the pump. The steps are generated regardless of the length of tubing 6 between the garments and the pump. The distance between the steps can be used to detect leaks or low pressure and therefore can be used as a feedback mechanism to set the correct inflation regime.

Figure 3:
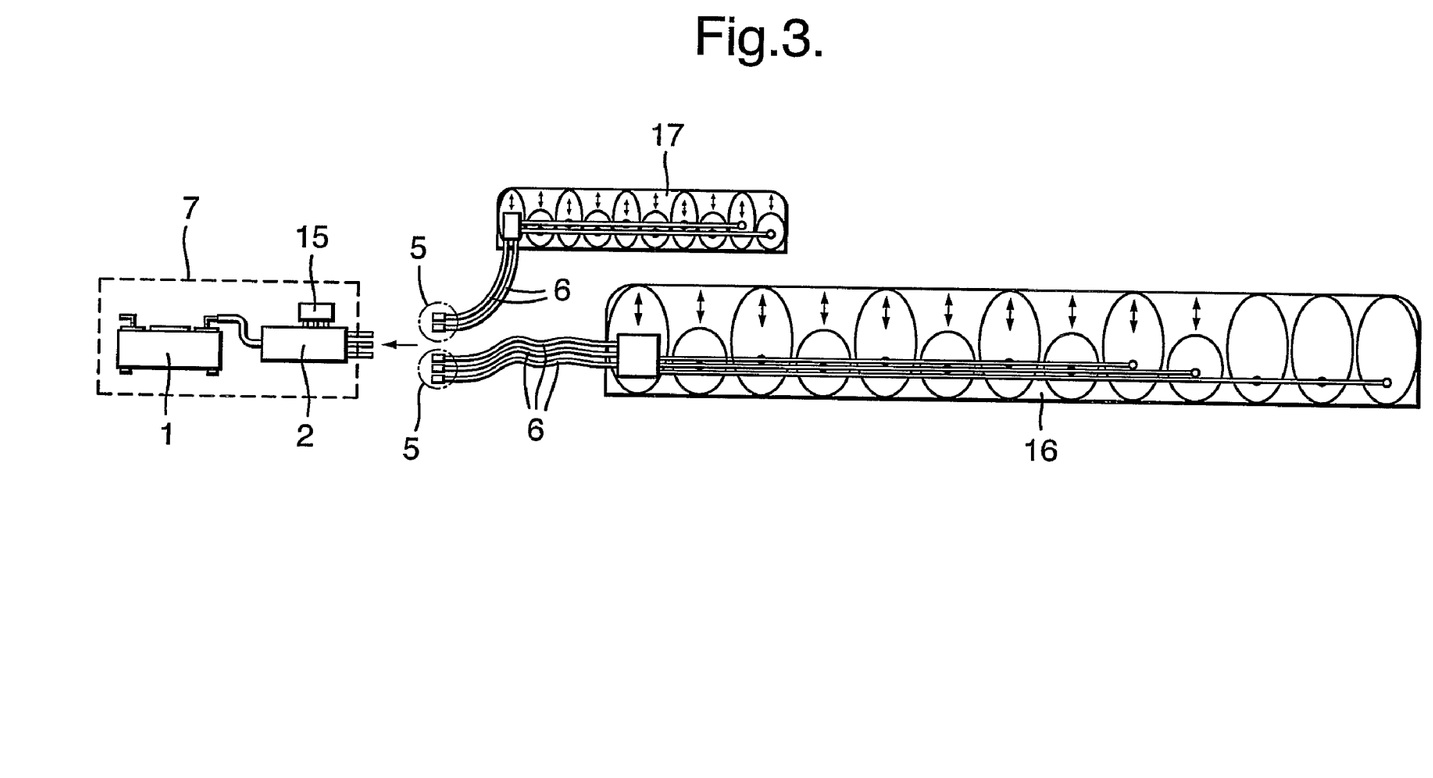
FIG. 3 is a schematic representation of another preferred embodiment of the invention.

Instead of the compression garments 3, 4 the pump can be used to supply pressurised air to a support surface as shown in FIG. 3. The same procedure applies and the pump recognises the support surface by means of the steps detected during initial inflation. With respect to the mattresses and cushions, the pump will be pre-set to supply different inflation and deflation cycles and pressures as appropriate. Similarly, the invention can be used where there is a requirement to automatically identify the article connected to a pump and apply the appropriate inflation regime with respect to the timings and pressure.

Although, the specific embodiments have shown the use of a flat valve as a means of generating the identifying pressure waveforms, there are other means of generating the same for example, small plastic balls, discs and reed valves and similar. The steps are generated before the article is inflated allowing the regime to be modified or stopped before the wrong therapy is applied.

The geometry of the chamber, vents sizes, flap material and flap design all have an affect on the operation of the identifying means and the means can be tuned for any particular flow regime desired.

The invention claimed is:

1. An inflatable article including:
    a. a flow path through which the inflatable article receives air, the flow path including a receiving end entering the inflatable article and an opposing supply end into which air is received;
    b. a valve situated along the flow path, wherein:
        (1) the valve receives air from the receiving end and supplies air to the supply end,
        (2) during an inflation cycle over which the inflatable article is inflated and then deflated, the valve interrupts air flow within the flow path;
    c. a sensor monitoring the pressure in the flow path, wherein the interruption of air flow generated by the valve generates a pressure signature detectable by the sensor, the pressure signature serving to identify the valve, and wherein the valve includes a vent to the atmosphere, wherein the vent is closed after a delay following the start of the inflation cycle.

2. The inflatable article of claim 1 further including a pump supplying air to the flow path, wherein the pump supplies air in accordance with the pressure signature of the valve.

3. The inflatable article of claim 2 further including a connector situated along the flow path, wherein:
    a. the connector removably connects the pump to the article, and
    b. the valve is situated within the connector.

4. The inflatable article of claim 1 wherein the interruption of air flow generated by the valve within the flow path occurs during the first 25% of an inflation cycle.

5. The inflatable article of claim 1 wherein the interruption of air flow generated by the valve within the flow path occurs over less than 25% of the inflation cycle.

6. An inflatable article including:
    a. a flow path through which the inflatable article receives air, the flow path including a receiving end entering the inflatable article and an opposing supply end into which air is received;
    b. a valve situated along the flow path, wherein:
        (1) the valve receives air from the receiving end and supplies air to the supply end,
        (2) during an inflation cycle over which the inflatable article is inflated and then deflated, the valve interrupts air flow within the flow path;
    c. a sensor monitoring the pressure in the flow path, wherein:
    A. the interruption of air flow generated by the valve generates a pressure signature detectable by the sensor, the pressure signature serving to identify the valve; and
    B. wherein the valve includes two or more vents to the atmosphere, wherein at least some of the vents are closed in succession during the course of the inflation cycle.

7. Two or more inflatable articles, each inflatable article including:
    a. a flow path through which the inflatable article receives air, the flow path including a receiving end entering the inflatable article and an opposing supply end into which air is received;
    b. a valve situated along the flow path, wherein:
        (1) the valve receives air from the receiving end and supplies air to the supply end,
        (2) during an inflation cycle over which the inflatable article is inflated and then deflated, the valve interrupts air flow within the flow path;
    c. a sensor monitoring the pressure in the flow path, wherein:
    A. the interruption of air flow generated by the valve generates a pressure signature detectable by the sensor, the pressure signature serving to identify the valve;
    B. each article has one or more inflatable chambers therein;
    C. the articles differ in one or more of:
        (i) their interior volume to be inflated, and
        (ii) their number of inflatable chambers; and
    D. each article has a valve generating a different pressure signature.

8. An inflatable article including:
    a. an inflatable chamber;
    b. a pump;
    c. a valve supplying air to the inflatable chamber from the pump, wherein:
        (1) during an inflation cycle over which the pump supplies air to the inflatable chamber, the valve provides obstruction to air flow between the pump and the inflatable chamber,
        (2) the obstruction varies during the course of the inflation cycle,
    d. a sensor:
        (1) measuring variations in air pressure arising from the obstruction, and
        (2) in communication with the pump,
    wherein the pump supplies air to the inflatable chamber in response to the pressure variations measured by the sensor, and wherein the valve includes a vent to the atmosphere, wherein the vent is closed after a delay following the start of the inflation cycle.

9. The inflatable article of claim 8 further including a connector situated between the pump and the inflatable chamber, wherein:
  a. the inflatable chamber is physically connected to the pump via the connector, with the physical connection being detachable and re-attachable at the connector, and
  b. the valve is situated within the connector.

10. The inflatable article of claim 8 wherein the interruption of air flow generated by the valve within the flow path occurs during the first 25% of an inflation cycle.

11. The inflatable article of claim 8 wherein the interruption of air flow generated by the valve within the flow path occurs over less than 25% of the inflation cycle.

12. An inflatable article including:
  a. an inflatable chamber;
  b. a pump;
  c. a valve supplying air to the inflatable chamber from the pump, wherein:
    (1) during an inflation cycle over which the pump supplies air to the inflatable chamber, the valve provides obstruction to air flow between the pump and the inflatable chamber,
    (2) the obstruction varies during the course of the inflation cycle,
  d. a sensor:
    (1) measuring variations in air pressure arising from the obstruction, and
    (2) in communication with the pump,
  wherein:
  A. the pump supplies air to the inflatable chamber in response to the pressure variations measured by the sensor; and
  B. the valve includes two or more vents to the atmosphere, wherein at least some of the vents are closed in succession during the course of the inflation cycle.

* * * * *